US00PP14721P2

(12) United States Plant Patent
Smith

(10) Patent No.: US PP14,721 P2
(45) Date of Patent: Apr. 20, 2004

(54) CHRYSANTHEMUM PLANT NAMED 'GOLDEN YOLYNN'

(50) Latin Name: *Chrysanthemum×morifolium*
Varietal Denomination: Golden Yolynn

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/396,679

(22) Filed: Mar. 25, 2003

(51) Int. Cl.[7] ..... A01H 5/00
(52) U.S. Cl. ..... Plt./289
(58) Field of Search ..... Plt./289, 287

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Golden Yolynn', characterized by its upright, outwardly spreading and mounded plant habit; freely branching habit; uniform and freely flowering habit; decorative-type inflorescences; golden yellow-colored inflorescences with bronze-colored centers; and natural season flowering in early October in the Northern Hemisphere.

1 Drawing Sheet

Botanical classification/cultivar designation: *Chrysanthemum×morifolium* cultivar Golden Yolynn.

BACKGROUND OF THE INVENTION

The present invention relates to a new and distinct cultivar of Chrysanthemum plant, botanically known as *Chrysanthemum×morifolium*, commercially known as a garden-type Chrysanthemum and hereinafter referred to by the name 'Golden Yolynn'.

The new cultivar is a product of a mutation induction program conducted by the Inventor in Alva, Fla. The objective of the program is to create new garden-type Chrysanthemum cultivars having inflorescences with desirable inflorescence forms, attractive floret colors and good garden performance.

The new Chrysanthemum originated by exposing unrooted cuttings of the Chrysanthemum cultivar Glowing Lynn, disclosed in U.S. Plant Pat. No. 10,038, to X-ray radiation in July, 1998 in Alva, Fla. Following the radiation treatment, the cuttings were rooted and terminal apices were removed to promote lateral branch development. After lateral branches from the pinch reached sufficient size, terminal cuttings were harvested, planted and flowered in a controlled environment in Alva, Fla. The new Chrysanthemum was discovered and selected by the Inventor as a single flowering plant within this population in January, 1999. The selection of this plant was based on its desirable inflorescence form, attractive ray floret color and good garden performance.

Asexual reproduction of the new cultivar by terminal cuttings taken in a controlled environment in Alva, Fla. since March, 1999, has shown that the unique features of this new Chrysanthemum are stable and reproduced true to type in successive generations.

SUMMARY OF THE INVENTION

The cultivar Golden Yolynn has not been observed under all possible environmental conditions. The phenotype may vary somewhat with variations in environment such as temperature, daylength and light, intensity, without, however, any variance in genotype.

The following traits have been repeatedly observed and are determined to be the unique characteristics of 'Golden Yolynn'. These characteristics in combination distinguish 'Golden Yolynn' as a new and distinct cultivar:

1. Upright, outwardly spreading and mounded plant habit.
2. Freely branching habit; dense and full plants.
3. Uniform and freely flowering habit.
4. Decorative-type inflorescences.
5. Golden yellow-colored inflorescences with bronze-colored centers.
6. Natural season flowering in early October in the Northern Hemisphere.

Plants of the new Chrysanthemum are most similar to plants of the the cultivar Glowing Lynn. In side-by-side comparisons conducted in Alva, Fla., plants of the new Chrysanthemum differed from plants of the cultivar Glowing Lynn in the following characteristics:

1. Plants of the new Chrysanthemum flowered about five days earlier than plants of the cultivar Glowing Lynn.
2. Ray florets of the new Chrysanthemum and the cultivar Glowing Lynn differed in color as ray florets of the cultivar Glowing Lynn were orange-bronze.

Plants of the new Chrysanthemum can also be compared to plants of the Chrysanthemum cultivar Legend, disclosed in U.S. Plant Pat. No. 6,404. In side-by-side comparisons conducted in Alva, Fla., plants of the new Chrysanthemum differed from plants of the cultivar Legend in the following characteristics:

1. Plants of the new Chrysanthemum were shorter and more mounded than plants of the cultivar Legend.
2. Plants of the new Chrysanthemum flowered about three weeks later than plants of the cultivar Legend.
3. Plants of the new Chrysanthemum had larger inflorescences than plants of the cultivar Legend.
4. Inflorescences of plants of the new Chrysanthemum had dark bronze centers whereas inflorescences of plants of the cultivar Legend did not have dark bronze centers.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Golden Yolynn'.

The photograph at the bottom of the sheet comprises a close-up view of typical inflorescences of the cultivar 'Golden Yolynn'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Salinas, Calif., under natural season conditions and practices which approximate those generally used in commercial garden-type Chrysanthemum production. One cutting was planted in a 15.25-cm container in late May, 2002. Plants were not pinched, that is, the terminal apex was not removed to enhance branching. During the production of the plants, day temperatures averaged 20° C. and night averaged 13° C. Measurements and numerical values represent averages for typical flowering plants.

Botanical classification: *Chrysanthemum×morifolium* cultivar Golden Yolynn.

Commercial classification: Decorative-type garden Chrysanthemum.

Parentage: Induced mutation of the *Chrysanthemum×morifolium* cultivar Glowing Lynn, disclosed in U.S. Plant Pat. No. 10,038.

Propagation:

*Type.*—Terminal tip cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Appearance.*—Perennial herbaceous decorative-type garden Chrysanthemum. Inverted triangle with rounded crown. Stems initially upright, then somewhat outwardly spreading giving a uniformly mounded appearance to the plant. Freely branching with lateral branches forming at every node.

*Plant height.*—About 23.5 cm.

*Plant diameter.*—About 39 cm.

*Lateral branches.*—Length: About 21 cm. Diameter: About 4.5 mm. Internode length: About 1.4 cm. Aspect: Upright and outwardly spreading. Texture: Pubescent. Color: 146A overlain with 187A.

*Foliage description.*—Leaf arrangement: Alternate. Length: About 4.3 cm. Width: About 3.6 cm. Apex: Mucronate. Base: Attenuate. Margin: Palmately lobed, sinuses divergent. Texture, upper surface: Slightly pubescent. Texture, lower surface: Pubescent; veins prominent. Color: Developing and fully expanded foliage, upper surface: Darker than 147A. Developing and fully expanded foliage, lower surface: Darker than 147B. Venation, upper surface: 147A to 147B. Venation, lower surface: 147B. Petiole length: About 1.1 cm. Petiole diameter: About 3 mm. Petiole color, upper and lower surfaces: Close to 147B.

Inflorescence description:

*Appearance.*—Decorative-type inflorescence form with elongated oblong-shaped ray florets. Inflorescences borne on terminals above foliage, arising from leaf axils. Disk and ray florets developing acropetally on a capitulum. About twelve inflorescences per lateral.

*Flowering response.*—Under natural season conditions, plants flower in early October in the Northern Hemisphere.

*Inflorescence bud (before showing color).*—Height: About 3 mm. Diameter: About 5.5 mm. Shape: Oblate. Color (lower surface of phyllaries): 147A.

*Inflorescence size.*—Diameter: About 3.7 cm. Depth (height): About 1.5 cm. Disc diameter: About 2 mm; inconspicious. Receptacle diameter: About 5 mm.

*Ray florets.*—Shape: Elongated oblong. Length: About 1.7 cm. Corolla tube length: About 2 mm. Width: About 5 mm. Apex: Acute to emarginate. Margin: Entire. Texture: Smooth, glabrous; satiny. Surface: Concave. Orientation: Initially upright, then perpendicular to vertical. Number of ray florets per inflorescence: About 171 in numerous whorls. Color: When opening, upper surface: Close to 9A overlain with 185A. When opening, lower surface: Close to 9C underlain with 185A. Opened inflorescence, upper surface: Close to 9A. Opened inflorescence, lower surface: Close to 9C.

*Disc florets.*—Shape: Tubular; apex dentate, five-pointed. Length: About 2.5 mm. Width, apex: About 1.25 mm. Width, base: About 1 mm. Number of disc florets per inflorescence: Less than five. Color: Immature: Close to 154D. Mature: Apex: 9A. Mid-section: Close to 150D. Base: Close to 155D.

*Peduncle.*—Strength: Strong. Aspect: About 45 to 50° from vertical. Length: First peduncle: About 5.4 cm. Fourth peduncle: About 8 cm. Seventh peduncle: About 10.8 cm. Diameter: About 3 mm. Texture: Pubescent. Color: 146A slightly overlain with 187A.

*Phyllaries.*—Quantity per inflorescence: About 52. Length: About 6 mm. Width: About 2 mm. Shape: Ligulate. Apex: Acute. Base: Truncate. Margin: Entire. Texture, upper surface: Smooth, waxy. Texture, lower surface: Pubescent. Color, upper surface: 146A. Color, lower surface: 147A.

*Reproductive organs.*—Androecium: Present on disc florets only. Anther color: 9A. Pollen: None observed. Gynoecium: Present on both ray and disc florets.

*Seed/fruit.*—Seed and fruit production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 37° C.

It is claimed:

1. A new and distinct cultivar of Chrysanthemum plant named 'Golden Yolynn', as illustrated and described.

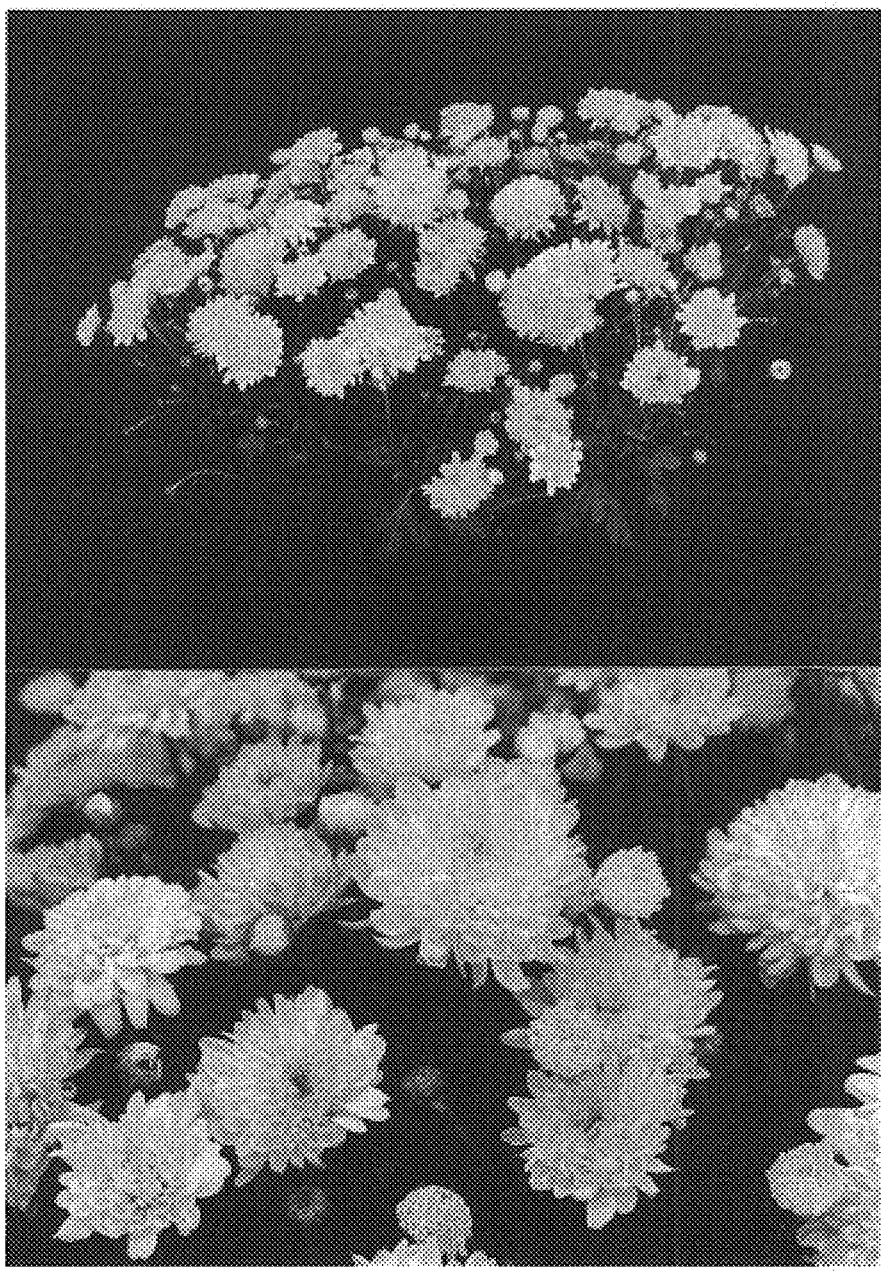

* * * * *